United States Patent
Scates et al.

(10) Patent No.: US 9,540,302 B2
(45) Date of Patent: Jan. 10, 2017

(54) PROCESSES FOR PRODUCING ACETIC ACID

(71) Applicant: Celanese International Corporation, Irving, TX (US)

(72) Inventors: Mark O. Scates, Houston, TX (US); Sarah Lane Abrego, Houston, TX (US); Yaw-Hwa Liu, Missouri City, TX (US); Ronald D. Shaver, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

(21) Appl. No.: 14/694,913

(22) Filed: Apr. 23, 2015

(65) Prior Publication Data
US 2016/0289153 A1 Oct. 6, 2016

Related U.S. Application Data

(60) Provisional application No. 62/141,490, filed on Apr. 1, 2015.

(51) Int. Cl.
 *C07C 51/47* (2006.01)
 *C07C 51/12* (2006.01)

(52) U.S. Cl.
 CPC ............. *C07C 51/12* (2013.01); *C07C 51/47* (2013.01)

(58) Field of Classification Search
 CPC .............................. C07C 51/72; C07C 51/47
 USPC ....................................................... 562/519
 See application file for complete search history.

(56) References Cited

U.S. PATENT DOCUMENTS

| 4,894,477 | A | 1/1990 | Scates et al. |
| 4,908,477 | A | 3/1990 | Hartmann et al. |
| 5,144,068 | A | 9/1992 | Smith et al. |
| 5,220,058 | A | 6/1993 | Fish et al. |
| 5,344,976 | A | 9/1994 | Jones et al. |
| 5,625,095 | A | 4/1997 | Miura et al. |
| 5,731,252 | A | 3/1998 | Warner et al. |
| 6,657,078 | B2 | 12/2003 | Scates et al. |
| 7,678,940 | B2 | 3/2010 | Miura et al. |
| 2009/0187043 | A1 | 7/2009 | Scates et al. |
| 2013/0116470 | A1 | 5/2013 | Miura et al. |
| 2013/0261334 | A1 | 10/2013 | Shimizu et al. |
| 2013/0264186 | A1 | 10/2013 | Shimizu et al. |
| 2013/0281735 | A1 | 10/2013 | Shimizu et al. |
| 2013/0303800 | A1 | 11/2013 | Shimizu |
| 2013/0310603 | A1 | 11/2013 | Shimizu et al. |

FOREIGN PATENT DOCUMENTS

| CN | 1349855 | 5/2002 |
| CN | 1640543 | 7/2005 |
| CN | 101053841 | 10/2007 |
| EP | 0087870 A1 | 9/1987 |
| JP | H8-20555 A | 1/1996 |
| JP | 2009-501129 A | 1/2009 |

OTHER PUBLICATIONS

Translation of Office Action dated Sep. 18, 2015 in corresponding Japanese Application No. JP2015-115653, 5 pages.
International Search Report received in the corresponding International Patent Application No. PCT/US2015/053737, dated Jan. 21, 2016, 11 pgs.

*Primary Examiner* — Sikarl Witherspoon
(74) *Attorney, Agent, or Firm* — Kilpatrick Townsend & Stockton LLP

(57) ABSTRACT

Processes for the producing acetic acid and, in particular, to improved processes for removing a cation, such as lithium, and iodides from a low energy carbonylation process to produce purified acetic acid. In one embodiment, the cation, e.g., lithium, may be removed using a cationic exchanger prior to removing iodides using a metal-exchanged ion exchange resin. The present invention is suited for removing at least one cation selected from the group consisting of Groups IA and IIA of the periodic table, quaternary nitrogen cations, and phosphorous-containing cations.

13 Claims, 2 Drawing Sheets

PROCESSES FOR PRODUCING ACETIC ACID

CROSS-REFERENCES TO RELATED APPLICATIONS

This patent application claims priority from U.S. Provisional Patent Application Ser. No. 62/141,490, entitled "Processes For Producing Acetic Acid", filed Apr. 1, 2015, the disclosure of which is incorporated herein by reference in its entirety.

FIELD OF THE INVENTION

This invention relates to processes for producing acetic acid and, in particular, to improved processes for removing lithium and iodides from a low energy carbonylation process to produce purified acetic acid.

BACKGROUND OF THE INVENTION

Among currently employed processes for synthesizing acetic acid, one of the most useful commercially is the catalyzed carbonylation of methanol with carbon monoxide as taught in U.S. Pat. No. 3,769,329, incorporated herein by reference in its entirety. The carbonylation catalyst contains rhodium, either dissolved or otherwise dispersed in a liquid reaction medium or supported on an inert solid, along with a halogen-containing catalyst promoter as exemplified by methyl iodide. The rhodium can be introduced into the reaction system in any of many forms. Likewise, because the nature of the halide promoter is not generally critical, a large number of suitable promoters, most of which are organic iodides, may be used. Most typically and usefully, the reaction is conducted by continuously bubbling carbon monoxide gas through a liquid reaction medium in which the catalyst is dissolved.

A widely used and successful commercial process for synthesizing acetic acid involves the catalyzed carbonylation of methanol with carbon monoxide. The catalyst contains rhodium and/or iridium and a halogen promoter, typically methyl iodide. The reaction is conducted by continuously bubbling carbon monoxide through a liquid reaction medium in which the catalyst is dissolved. The reaction medium comprises acetic acid, methyl acetate, water, methyl iodide and the catalyst. Commercial processes for the carbonylation of methanol include those described in U.S. Pat. No. 3,769,329, the entireties of which is incorporated herein by reference. Another conventional methanol carbonylation process includes the Cativa™ process, which is discussed in Jones, J. H. (2002), "*The Cativo™ Process for the Manufacture of Acetic Acid*," Platinum Metals Review, 44 (3): 94-105, the entirety of which is incorporated herein by reference.

The AO™ process for the carbonylation of an alcohol to produce the carboxylic acid having one carbon atom more than the alcohol in the presence of a rhodium catalyst is disclosed in U.S. Pat. Nos. 5,001,259; 5,026,908; and 5,144,068; and EP0161874, the entireties of which are incorporated herein by reference. As disclosed therein, acetic acid is produced from methanol in a reaction medium containing methyl acetate (MeAc), methyl halide, especially methyl iodide (MeI), and rhodium present in a catalytically effective concentration. These patents disclose that catalyst stability and the productivity of the carbonylation reactor can be maintained at high levels, even at very low water concentrations, i.e., 4 weight percent or less, (despite the prior practice of maintaining approximately 14-15 wt. % water) by maintaining in the reaction medium, along with a catalytically effective amount of rhodium, at least a finite concentration of water, e.g., 0.1 wt. %, and a specified concentration of iodide ions over and above the iodide ion that is present as hydrogen iodide. This iodide ion is a simple salt, with lithium iodide being preferred. The salt may be formed in situ, for example, by adding lithium acetate, lithium carbonate, lithium hydroxide or other lithium salts of anions compatible with the reaction medium. The patents teach that the concentration of methyl acetate and iodide salts are significant parameters in affecting the rate of carbonylation of methanol to produce acetic acid, especially at low reactor water concentrations. By using relatively high concentrations of the methyl acetate and iodide salt, a high degree of catalyst stability and reactor productivity is achieved even when the liquid reaction medium contains water in finite concentrations as low as 0.1 wt. %. Furthermore, the reaction medium employed improves the stability of the rhodium catalyst, i.e., resistance to catalyst precipitation, especially during the product recovery steps of the process. In these steps, distillation for the purpose of recovering the acetic acid product tends to remove from the catalyst the carbon monoxide, which in the environment maintained in the reaction vessel, is a ligand with stabilizing effect on the rhodium.

U.S. Pat. No. 5,144,068, the entirety of which is incorporated herein by reference, discloses a process for producing acetic acid by reacting methanol with carbon monoxide in a liquid reaction medium containing a rhodium (Rh) catalyst and comprising water, acetic acid, methyl iodide, and methyl acetate, wherein catalyst stability is maintained in the reaction by maintaining in said reaction medium during the course of said reaction 0.1 wt. % to less than 14 wt. % of water together with (a) an effective amount in the range of 2 wt. % to 20 wt. % of a catalyst stabilizer selected from the group consisting of iodide salts which are soluble in said reaction medium in effective concentration at reaction temperature, (b) 5 wt. % to 20 wt. % of methyl iodide, and (c) 0.5 wt. % to 30 wt. % of methyl acetate. Suitable iodide salts may be a quaternary iodide salt or an iodide salt of a member of the group consisting of the metals of Group IA and Group IIA of the Periodic Table.

Carbonyl impurities, such as acetaldehyde, that are formed during the carbonylation of methanol may react with iodide catalyst promoters to form multi-carbon alkyl iodides, e.g., ethyl iodide, propyl iodide, butyl iodide, pentyl iodide, hexyl iodide, and the like. It is desirable to remove multi-carbon alkyl iodides from the reaction product because even small amounts of these impurities in the acetic acid product tend to poison the catalyst used in the production of vinyl acetate, a product commonly produced from acetic acid.

Conventional techniques to remove such impurities include treating the crude acid product streams with oxidizers, ozone, water, methanol, activated-carbon, amines, and the like. Such treatments may or may not be combined with distillation of the acetic acid. The most typical purification treatment involves a series of distillations of the final product. It is also known to remove carbonyl impurities from organic streams by treating the organic streams with an amine compound such as hydroxylamine, which reacts with the carbonyl compounds to form oximes, followed by distillation to separate the purified organic product from the oxime reaction products. However, the additional treatment of the final product adds cost to the process, and distillation of the treated acetic acid product can result in additional impurities being formed.

While it is possible to obtain acetic acid of relatively high purity, the acetic acid product formed by the low-water carbonylation process and purification treatment described above frequently remains somewhat deficient with respect to the permanganate time due to the presence of small proportions of residual impurities. Because a sufficient permanganate time is an important commercial test, which the acid product may be required to meet to be suitable for many uses, the presence of impurities that decrease permanganate time is objectionable. Moreover, it has not been economically or commercially feasible to remove minute quantities of these impurities from the acetic acid by distillation because some of the impurities have boiling points close to that of the acetic acid product or halogen-containing catalyst promoters, such as methyl iodide. It has thus become important to identify economically viable methods of removing impurities elsewhere in the carbonylation process without contaminating the final product or adding unnecessary costs.

Macroreticulated or macroporous strong acid cationic exchange resin compositions are conventionally utilized to reduce iodide contamination. Suitable exchange resin compositions, e.g., the individual beads thereof, comprise both sites that are functionalized with a metal, e.g., silver, mercury or palladium, and sites that remain in the acid form. Exchange resin compositions that have little or no metal-functionality do not efficiently remove iodides and, as such, are not conventionally used to do so. Typically, metal-functionalized exchange resins are provided in a fixed bed and a stream comprising the crude acetic acid product is passed through the fixed resin bed. In the metal functionalized resin bed, the iodide contaminants contained in the crude acetic acid product are removed from the crude acid product stream.

U.S. Pat. No. 6,657,078 describes a low-water process that uses a metal-functionalized exchange resin to remove iodides. The reference also avoids the use of a heavy ends column, resulting in an energy savings.

The metal-functionalization of exchange resin compositions often involves significant processing and expense, often costing orders of magnitude more than resins that are not metal-functionalized. Often the process steps associated with the functionalization varies very little with regard to the actual amount of metal that is deposited on the exchange resin. For example, the processing necessary to functionalize 50% of the active sites of a quantity of exchange resin is quite similar to the processing necessary to functionalize 10% of the active sites of the same quantity of exchange resin. Because the entire quantity of exchange resin requires processing, however, both the 50%-functionalized exchange resin and the 10%-functionalized resin require significantly more processing than the same quantity of non-functionalized resin.

Other ion exchange resins have been used to remove iodide impurities from acetic acid and/or acetic anhydride. There is disclosed in U.S. Pat. No. 5,220,058 the use of ion exchange resins having metal exchanged thiol functional groups for removing iodide impurities from acetic acid and/or acetic anhydride. Typically, the thiol functionality of the ion exchange resin has been exchanged with silver, palladium, or mercury.

In addition to iodide contaminants, metals from the walls of the vessels used in the acetic acid production system often corrode and dissolve into the crude acetic acid product compositions. Thus, conventional crude acid product streams often comprise corrosion metal contaminants as well as iodide contaminants. These corrosion metals are known to interfere with the carbonylation reaction or accelerate competing reactions such as the water-gas shift reaction. Typically, these corrosion metals may be removed from the process streams by passing the streams through resin beds comprising standard macroreticular or macroporous cationic exchange resins.

In a case where a silver, mercury or palladium exchanged resin is utilized, however, the soluble corrosion metal cations may detrimentally displace the metal-functionalized sites of the exchange resins. As such, these exchange sites are unable to capture/remove the iodide contaminants. The lifetime of the functionalized resin, with regard to iodide removal, is shortened by the presence of corrosion metals. Often a pre-determined portion of the sites of the exchange resin composition are functionalized, thus leaving the remainder of the sites in the acid form As a result, the acid sites capture much of the corrosion metals while many of the functionalized sites remain available for iodide removal. Although this technique may improve the lifetime of exchange resins, the partial functionalization of the pre-determined portion of sites requires significant processing and resources.

In addition, it has been found that a problem associated with the use of silver-exchanged strong acid cation exchange resins is that the silver may actually be displaced by corrosion metals, as described in U.S. Pat. No. 5,344,976. The patent describes the use of a cation exchanger in the acid form to remove at least a portion of the metal ion contaminants such as iron, potassium, calcium, magnesium, and sodium from a carboxylic acid stream prior to contacting the stream with the exchanged strong acid cation exchange resin to remove $C_1$ to $C_{10}$ alkyl iodide compounds, hydrogen iodide or iodide salts. However, this process does not describe purification for low-energy and low-water carbonylation processes as described above that may contain lithium and larger alkyl iodide compounds, in addition to iodides.

In addition, other schemes introduce other contaminants that may need to be removed from the product. For example, it has been well known in the art for some time that adding an alkali component such as KOH to the drying column of a carbonylation purification process is useful to inhibit the buildup of HI in the column. See, e.g., US 2013/0264186 and earlier references. However, this addition introduces a potassium cation into the process that can also displace the silver in a silver-exchanged strong acid cation exchange resin.

Other processes remove corrosion metal contaminants at different stages of the process, for example from the reactant composition. U.S. Pat. No. 4,894,477 describes a process that uses strongly acidic ion exchange resins in the lithium form to remove corrosion metal contaminants. U.S. Pat. No. 5,731,252 describes contacting the catalyst solution with an ion exchange resin bed, in the lithium form, while requiring simultaneous addition of a sufficient amount of water to allow the corrosion metal salts in the catalyst medium to dissociate so that ion exchange can occur and the corrosion metals can be removed from the reactor catalyst solution.

While the above-described processes have been successful, the need exists for process for improved processes for producing acetic acid, in particular, low water and low energy processes and methods for removing contaminants from those processes.

SUMMARY OF THE INVENTION

This invention relates to processes for the production of acetic acid. In a first aspect, the present invention relates to process for producing acetic acid comprising carbonylating at least one member selected from the group consisting of methanol, dimethyl ether, and methyl acetate in the presence of 0.1 to less than 14 wt. % water, a rhodium catalyst, methyl iodide and iodide salts, to form a reaction medium in a reactor, separating the reaction medium into a liquid recycle stream and a vapor product stream, and separating the vapor product stream in up to 2 distillation columns in a primary purification train, preferably two distillation columns, to produce a crude acid product comprising acetic acid comprising at least one cation selected from the group consisting of Groups IA and HA of the periodic table, and preferably lithium and potassium, quaternary nitrogen cations and phosphorous-containing cations. The cations may be formed in-situ in the carbonylation reactor through the use of organic salts, ligands, or other catalyst promoters. The crude acetic acid product may be essentially anhydrous, e.g., having less than 0.2 wt. % water. The process further comprises contacting the crude acetic acid product with a cationic exchanger in the acid form to produce an intermediate acid product and contacting the intermediate acetic acid product with a metal-exchanged ion exchange resin having acid cation exchange sites to produce a purified acetic acid. The amount of the at least one cation may vary and for example may be up to 10 ppm lithium, based on the total weight of the crude acid product. After contacting with the cationic exchanger, the intermediate acetic acid product may have a lithium ion concentration of less than 50 ppb. The cationic exchanger in the acid form comprises a resin of acid-form strong acid cation exchange macroreticular, macroporous or mesoporous resins. The metal-exchanged ion exchange resin may comprise at least one metal selected from the group consisting of silver, mercury, palladium and rhodium. In one embodiment, at least 1% of the strong acid exchange sites of said metal-exchanged resin are occupied by silver. In another embodiment, at least 1% of the strong acid exchange sites of said metal-exchanged resin are occupied by mercury. The process may further comprise treating the purified acetic acid product with a cationic exchange resin to recover any silver, mercury, palladium or rhodium.

In one embodiment, prior to contacting the crude acetic acid product with the cationic exchanger, the process may adjust the temperature of the crude acetic acid product to from 50° C. to 120° C. Also, prior to contacting the intermediate acetic acid product with a metal-exchanged ion exchange resin, the process may adjust the temperature of the intermediate acetic acid product to from 50° C. to 85° C. In a further embodiment, the process further comprises a step of adding a potassium salt selected from the group consisting of potassium acetate, potassium carbonate, and potassium hydroxide to the distilled acetic acid product prior to distilling the distilled acetic acid product in a second distillation column. At least a portion of the potassium may be removed by the cationic exchanger in the acid form.

In one embodiment, separating the vapor product stream may comprise distilling the vapor product stream in a first distillation column and taking a sidedraw to yield a distilled acetic acid product, and distilling the distilled acetic acid product in a second distillation column to produce a crude acid product comprising acetic acid and cations selected from the group consisting of Groups IA and IIA of the periodic table, quaternary nitrogen cations, phosphorous-containing cations. The crude acid product may be removed from a side stream port at a position above the bottom of the second distillation column. In another embodiment, the crude acid product may be removed as a residue from the bottom of the second distillation column.

In a second aspect, the present invention relates to process for removing iodides from a liquid composition comprising a carboxylic acid or an anhydride thereof, greater than 10 ppb of $C_{10}$-$C_{14}$ alkyl iodides, iodide anions, and a cation selected from the group consisting of Group IA and IIA metals, quaternary nitrogen cations, and quaternary phosphorous-containing cations. Preferably the cation comprises lithium. In one embodiment, the liquid composition may be essentially anhydrous, e.g. having less than 0.2 wt. % water. The process comprises contacting said liquid composition with a cationic exchanger in the acid form to produce an intermediate product with a reduced concentration of cations selected from the group consisting of Group IA and IIA metals, quaternary nitrogen cations, quaternary phosphorous-containing cations and contacting the intermediate product with a metal-exchanged ion exchange resin having acid cation exchange sites comprising at least one metal selected from the group consisting of silver, mercury, palladium and rhodium to produce a purified acetic acid product. The amount of the at least one cation may vary and for example may be up to 10 ppm lithium, based on the total weight of the crude acid product. After contacting with the cationic exchanger, the intermediate acetic acid product may have a lithium ion concentration of less than 50 ppb. The cationic exchanger in the acid form comprises a resin of acid-form strong acid cation exchange macroreticular, macroporous or mesoporous resins. The metal-exchanged ion exchange resin may comprise at least one metal selected from the group consisting of silver, mercury, palladium and rhodium. In one embodiment, at least 1% of the strong acid exchange sites of said metal-exchanged resin are occupied by silver. In another embodiment, at least 1% of the strong acid exchange sites of said metal-exchanged resin are occupied by mercury.

BRIEF DESCRIPTION OF THE DRAWINGS

The present invention will be better understood in view of the appended non-limiting figures, wherein.

DETAILED DESCRIPTION OF THE INVENTION

Introduction

Figure 1:
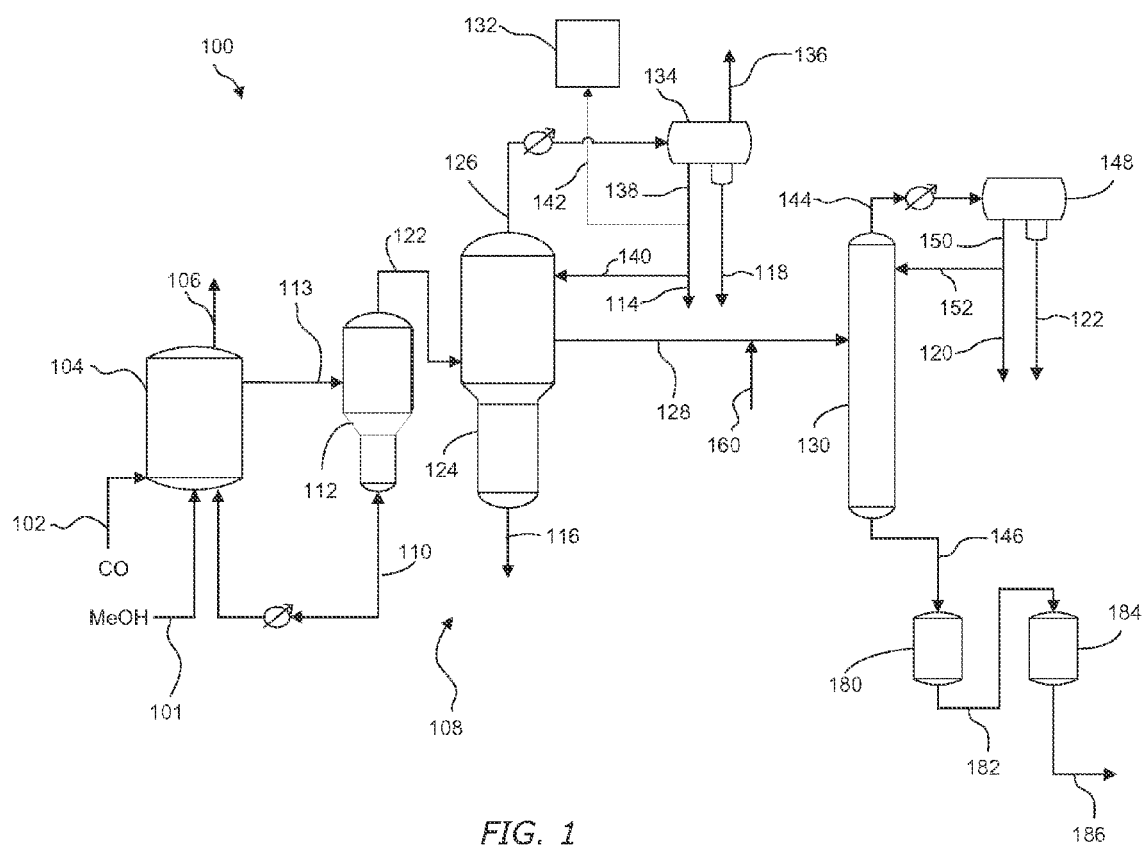
FIG. 1 illustrates a process for producing acetic acid with a metal functionalized fixed resin bed for iodide removal.

This invention relates to processes for the production of acetic acid and, in particular, to improved processes for removing cations, such as lithium, and iodides, including higher molecular weight iodides, for example, $C_{10}$-$C_{14}$ alkyl iodides, from a low energy carbonylation process. The process is capable of removing at least one cation selected from the group consisting of Groups IA and IIA of the periodic table, quaternary nitrogen cations, and phosphorous-containing cations. According to the present invention the cation is removed prior to the iodide removal.

With ever increasing cost pressures and higher energy prices, there has been ever increasing motivation to simplify chemical manufacturing operations and particularly to reduce the number of manufacturing steps. In this regard, it is noted that U.S. Pat. No. 5,416,237 discloses a single zone distillation process for making acetic acid. Such process modifications, while desirable in terms of energy costs, tend to place increasing demands on the purification train. In particular, fewer recycles and distillations tend to introduce (or fail to remove) a higher level of iodides and other promoters in the crude acid product, and particularly more iodides of a higher molecular weight. For example, octyl iodide, decyl iodide and dodecyl iodides may all be present in the crude acid product as well as hexadecyl iodide; all of which are difficult to remove by conventional techniques.

Low water and low energy processes for producing acetic acid by the carbonylation of methanol have been developed which involve a rhodium-catalyzed system operating at less than 14 wt. % water and utilizing up to 2 distillation columns in the primary purification train. The primary purification train is directed at removing bulk components, such as water, methyl acetate, methyl iodide, and hydrogen iodide, from the vapor product stream from the reactor/flasher to obtain acetic acid. This primary purification train receives the majority of the vapor flow from the reactor and obtains acetic acid as a final product. For example, the columns of the primary purification train include the light ends column and drying column. This primary purification train may exclude columns whose main function is to remove minor components such as acetaldehyde, alkanes, and propionic acid.

The process for producing acetic acid may generate a cation that is collected in the crude acid product. These residual cations may be difficult to remove and in the final metal-exchange guard bed may adversely replace iodides. Thus, the final product may have unacceptable levels of iodides despite using a metal exchange guard bed. The present invention provides process for removing the cations.

The source of the cation may come from a variety promoters, co-catalysts, additives, in situ reactions, etc. For example low water and low energy processes that involve the use of a promoter such as lithium iodide, which may form in situ following the addition of lithium acetate or other compatible lithium salts to the reaction mixture. Therefore, process streams may contain some quantity of lithium ions. In addition, since the process uses a maximum of 2 distillation columns in the primary purification train and preferable the primary purification does not include a column to remove heavy ends materials, the crude acid product may contain larger alkyl iodide compounds, e.g., $C_{10}$-$C_{14}$ alkyl iodides, in addition to cations, such as lithium. Sometimes more than 10% of the iodides present, or even more than 50%, have an organic chain length of more than 10 carbon atoms. Thus, there may be more than 10 ppb, e.g., more than 20 ppb, more than 50 ppb, more than 100 ppb, or more than 1 ppm of $C_{10}$-$C_{14}$ alkyl iodides. These higher alkyl iodides may be in addition to the usual shorter chain length iodide impurities found in the crude acid product of an iodide promoted carbonylation process, including methyl iodide, HI, and hexyl iodide. The usual iodide impurities are typically removed from the crude acid product using a metal-exchanged strong acid ion exchange resin in which the metal is silver or mercury, for example. However, it has been found that the silver or mercury in the metal-exchanged strong acid ion exchange resin may be displaced by the residual lithium, resulting in lower resin capacity and efficiency and the potential for contaminating the product with silver or mercury.

The cation in the crude acid product may result from the use of organic alkali salt ligands, such as organic lithium salt ligands, such as those described CN101053841 and CN1349855, the entire contents and disclosure of which are hereby incorporated by reference. CN101053841 describes a ligand comprising lithium acetate or lithium oxalate. CN1349855 describes a bimetallic catalyst having a metal lithium organic ligand coordinating cis-dicarbonyl rhodium structure. The metal lithium organic ligand may be a pyridine derivative, such as lithium pyridine-2-formate, lithium pyridine-3-formate, lithium pyridine-4-formate, lithium pyridine-3-acetate, lithium pyridine-4-acetate, or lithium pyridine-3-propionate. In fact, the lithium salt component of all of these ligands are believed to generate lithium iodide in situ within the reaction medium after exposure to methyl iodide at reaction temperature and pressure in the carbonylation reactor. At least some small portion of the lithium component will entrain into the purification system. Thus, the present invention may also remove lithium formed in situ from use of these types of organic ligands.

Cations may also be present as a result of the use of non-lithium salts, such as through the use of bimetallic Rh chelating catalysts that have an amine functionality, such as those described in CN1640543, the entire contents and disclosure of which is hereby incorporated by reference. According to CN16040543 the cation species contains N and O donor atoms and is formed from aminobenzoic acid. The amine may quaternize with methyl iodide in situ within the reaction medium at reaction temperature and pressure to form a quaternary nitrogen cation. The quaternary nitrogen cation, similar to the lithium cation, may be carried through with the crude acid product and may be removed using the present invention prior to the metal-exchange guard beds.

The present invention therefore involves a low water and low energy process for producing acetic acid by the carbonylation of methanol, dimethyl ether, and/or methyl acetate in the presence of 0.1 to less than 14 wt. % water, a metal catalyst, methyl iodide and lithium iodide. The invention utilizes up to 2 distillation columns in the primary purification train and purifies the resulting acidic acid product with a cationic exchanger in the acid form to remove residual lithium ions followed by treatment with a metal-exchanged ion exchange resin having acid cation exchange sites comprising at least one metal selected from the group consisting of silver, mercury, palladium and rhodium The metal-exchanged ion exchange resin can have at least 1% of the strong acid exchange sites occupied by silver, mercury, palladium, and/or rhodium, e.g., at least 1% silver, mercury, palladium, and/or rhodium, at least 5% silver, mercury, palladium, and/or rhodium, at least 10% silver, mercury, palladium, and/or rhodium, or at least 20% silver, mercury, palladium, and/or rhodium. By using a cation exchanger to remove lithium prior to the use of a resin having metal-exchanged strong acid cation sites, the displacement of silver, mercury, palladium and/or rhodium from the metal-exchanged sites by the lithium is reduced or eliminated for a process that utilizes up to 2 distillation columns in the primary purification train.

Particularly preferred processes are those utilizing a cation exchanger for removing lithium followed by a silver-exchanged cationic substrate for removing iodides. The crude acid product in many cases includes organic iodides with a $C_{10}$ or more aliphatic chain length which need to be removed. Sometimes more than 10% of the iodides present, e.g., more than 30% or even more than 50%, have an organic chain length of more than 10 carbon atoms.

Decyl iodides and dodecyl iodides are especially prevalent in the absence of heavy ends and other finishing apparatus and are difficult to remove from the product. The silver-exchanged cationic substrates of the present invention typically remove over 90% of such iodides; oftentimes the crude acid product has from 10 to 1000 ppb total iodide prior to treatment which would make the product unusable for iodide-sensitive applications.

An iodide level of 20 ppb to 1.5 ppm in the crude acid product prior to iodide removal treatment is typical; whereas the iodide removal treatment is preferably operative to remove at least about 95% of the total iodide present. In a typical embodiment, lithium/iodide removal treatment involves contacting the crude acid product with a cation exchanger to remove 95% or more of the lithium ions followed by contacting the crude acid product with a silver-exchanged sulfonic acid functionalized macroreticular ion exchange resin, wherein the product has an organic iodide content of greater than 100 ppb prior to treatment and an organic iodide content of less than 10 ppb after contacting the resin.

Lithium has also been found to be entrained in the crude acid product in the absence of heavy ends and other finishing apparatus. Even in very small amounts of 10 ppb of lithium in the crude acid product may cause problem for removing iodides. Up to 10 ppm of lithium by weight of the crude acid product, e.g., up to 5 ppm, up to 1 ppm, up to 500 ppb, up to 300 ppb, or up to 100 ppb, might be present in the acid-containing crude acid product exiting the drying column of an acetic acid process, e.g., the last column in the primary purification train. In terms of ranges, there may be from 0.01 ppm to 10 ppm lithium in the crude acid product, e.g., from 0.05 ppm to 5 ppm or from 0.05 ppm to 1 ppm. By utilizing a cationic exchanger in the acid form before introducing the crude acid product to a metal-exchanged resin, significant amounts of lithium can be removed. For example greater than 90 wt. % of the lithium in the stream might be removed by the cationic exchanger, e.g. 95 wt. % or 99 wt. %. Thus, the stream exiting the acid-form cationic exchanger may contain less than 50 ppb lithium, e.g., less than 10 ppb, or less than 5 ppb. Such removal of the lithium can greatly extend the life of the metal-exchanged resin.

Acetic Acid Production Systems

An exemplary acetic acid production process is described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The purification processes described herein may be useful in carbonylation processes that use methanol and/or methyl acetate (MeAc), methyl formate or dimethyl ether, or mixtures thereof, to produce acetic acid in the presence of a Group VIII metal catalyst, such as rhodium, and a halogen-containing catalyst promoter. A particularly useful process is the low water rhodium-catalyzed carbonylation of methanol to acetic acid as exemplified in U.S. Pat. No. 5,001,259. Other metal catalysts, e.g., iridium-based catalysts, are contemplated as well.

Generally, the metal component, e.g., rhodium component, of the catalyst system is believed to be present in the form of a coordination compound of rhodium with a halogen component providing at least one of the ligands of such coordination compound. In addition to the coordination of rhodium and halogen, it is also believed that carbon monoxide will coordinate with rhodium. The rhodium component of the catalyst system may be provided by introducing into the reaction zone rhodium in the form of rhodium metal, rhodium salts such as the oxides, acetates, iodides, carbonates, hydroxides, chlorides, etc., or other compounds that result in the formation of a coordination compound of rhodium in the reaction environment.

The metal catalyst may comprise a Group VIII metal. Suitable Group VIII catalysts include rhodium and/or iridium catalysts. When a rhodium catalyst is used, the rhodium catalyst may be added in any suitable form such that rhodium is in the catalyst solution as an equilibrium mixture including $[Rh(CO)_2I_2]$-anion, as is well known in the art. Iodide salts optionally maintained in the reaction mixtures of the processes described herein may be in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; 5,144,068 and 7,005,541, the entireties of which are hereby incorporated by reference. The carbonylation of methanol utilizing iridium catalyst is well known and is generally described in U.S. Pat. Nos. 5,942,460, 5,932,764, 5,883,295, 5,877,348, 5,877,347 and 5,696,284, the entireties of which are hereby incorporated by reference.

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide.

The components of the reaction medium are maintained within defined limits to ensure sufficient production of acetic acid. The reaction medium contains a concentration of the metal catalyst, e.g. rhodium catalyst, in an amount from 200 to 3000 wppm, e.g., from 500 to 2000 wppm, or from 600 to 1500 wppm. The concentration of water in the reaction medium is maintained under low water conditions, e.g., less than 14% water, from 0.1 wt. % to less than 14 wt. %, from 0.2 wt. % to 10 wt. % or most preferably from 0.25 wt. % to 5 wt. %. The concentration of methyl iodide in the reaction medium is maintained to be from 1 to 25 wt. %, e.g., from 5 to 20 wt. %, from 4 to 13.9 wt. %. The concentration of iodide salt, e.g., lithium iodide, in the reaction medium is maintained to be from 1 to 25 wt. %, e.g., from 2 to 20 wt. %, from 3 to 20 wt. %. The concentration of methyl acetate in the reaction medium is maintained to be from 0.5 to 30 wt. %, e.g., from 0.3 to 20 wt. %, from 0.6 to 4.1 wt. %. The following amounts are based on the total weight of the reaction medium. The ranges disclosed in this application include the endpoints, subranges and individual values unless otherwise stated.

The concentration of acetic acid in the reaction medium is generally more than 30 wt. %, e.g. more than 40 wt. % or more than 50 wt. %.

In some embodiments, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters.

The carbonylation reaction of methanol to acetic acid product may be carried out by contacting the methanol feed with gaseous carbon monoxide bubbled through an acetic acid solvent reaction medium containing the rhodium catalyst, methyl iodide (MeI) promoter, methyl acetate (MeAc), and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion concentration is from 1 to 25 wt. % and the methyl acetate is generally present in amounts from 0.5 to 30 wt. %, and the methyl iodide is generally present in amounts from 1 to 25 wt. %. The rhodium catalyst is generally present in amounts from 200 to 3000 ppm.

Typical reaction temperatures for carbonylation will be from 150 to 250° C., with the temperature range of 180 to 225° C. being a preferred range. The carbon monoxide partial pressure in the reactor can vary widely but is typically from 2 to 30 atm, e.g., from 3 to 10 atm. The hydrogen partial pressure in the reactor is typically from 0.05 to 2 atm, e.g., from 1 to 1.9 atm. Because of the partial pressure of by-products and the vapor pressure of the contained liquids, the total reactor pressure will range from 15 to 40 atm. The production rate of acetic acid may be from 5 to 50 mol/L·h, e.g., from 10 to 40 mol/L·h, and preferably 15 to 35 mol/L·h.

Exemplary reaction and acetic acid recovery system 100 is shown in FIG. 1. As shown, methanol-containing feed stream 101 and carbon monoxide-containing feed stream 102 are directed to liquid phase carbonylation reactor 104, in which the carbonylation reaction occurs to form acetic acid.

Carbonylation reactor 104 is preferably either a stirred vessel or bubble-column type vessel, with or without an agitator, within which the reacting liquid or slurry contents are maintained, preferably automatically, a predetermined level, which preferably remains substantially constant during normal operation. Into carbonylation reactor 104, fresh methanol, carbon monoxide, and sufficient water are continuously introduced as needed to maintain suitable concentrations in the reaction medium.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. Gaseous purge stream 106 desirably is vented from the reactor 104 to prevent buildup of gaseous by-products and to maintain a set carbon monoxide partial pressure at a given total reactor pressure. The temperature of the reactor may be controlled and the carbon monoxide feed is introduced at a rate sufficient to maintain the desired total reactor pressure. Stream 113 comprising the liquid reaction medium exits reactor 104.

The acetic acid production system preferably includes primary purification train 108 employed to recover the acetic acid and recycle catalyst solution, methyl iodide, methyl acetate, and other system components within the process. Primary purification train 108 include light ends column 124 and drying column 130, and the associated pumps, overhead receivers, condensers, etc. Thus, a recycled catalyst solution, such as stream 110 from flasher 112, and optionally one or more of recycle streams 114, 116, 118, and 120, also are introduced into the reactor 104. Of course, one or more of the recycle streams may be combined prior to being introduced into the reactor. The separation system also preferably controls water and acetic acid content in the carbonylation reactor, as well as throughout the system, and facilitates PRC removal.

The reaction medium is drawn off from the carbonylation reactor 104 at a rate sufficient to maintain a constant level therein and is provided to flasher 112 via stream 113. In flasher 112, the crude product is separated in a flash separation step to obtain a vapor product stream 122 comprising acetic acid and less volatile stream 110 comprising a catalyst-containing solution (predominantly acetic acid containing the rhodium and the iodide salt along with lesser quantities of methyl acetate, methyl iodide, and water), which preferably is recycled to the reactor, as discussed above. The vapor product stream 122 also comprises methyl iodide, methyl acetate, water, and permanganate reducing compounds (PRC's). Dissolved gases exiting the reactor and entering the flasher comprise a portion of the carbon monoxide and may also contain gaseous by-products such as methane, hydrogen, and carbon dioxide. Such dissolved gases exit the flasher as part of the overhead stream. The overhead stream from flasher 112 is directed to the light ends column 124 as vapor product stream 122, where distillation yields a low-boiling overhead vapor stream 126, a sidedraw 128 that contains acetic acid, and a high boiling residue stream 116. Acetic acid removed via sidedraw 128 preferably is subjected to further purification, such as in drying column 130 for selective separation of acetic acid from water.

It has been disclosed in U.S. Pat. Nos. 6,143,930 and 6,339,171 that there is generally a higher concentration of the PRC's, and in particular acetaldehyde content, in the low-boiling overhead vapor stream exiting the light ends column than in the high-boiling residue stream exiting the column. Thus, in some cases, a portion of low-boiling overhead vapor stream 126, containing PRC's, is subjected to additional processing in a PRC removal system (PRS) 132 to reduce and/or remove the amount of PRC's present. As shown, low-boiling overhead vapor stream 126, therefore, is condensed and directed to an overhead phase separation unit, as shown by overhead receiver decanter 134. In addition to PRC's, low-boiling overhead vapor stream 126 will typically contain methyl iodide, methyl acetate, acetic acid, and water. For purposes of the present invention, primary purification train 108 does not include PRS 132.

Conditions are desirably maintained in the process such that low-boiling overhead vapor stream 126, once in decanter 134, will separate into a light phase and a heavy phase. Generally, low-boiling overhead vapor stream 126 is cooled to a temperature sufficient to condense and separate the condensable methyl iodide, methyl acetate, acetaldehyde and other carbonyl components, and water into two phases. A portion of stream 126 may include noncondensable gases such as carbon monoxide, carbon dioxide, hydrogen, and the like that can be vented as shown by stream 136 in FIG. 1, which may be directed to a low pressure absorber unit (not shown).

The condensed light phase in decanter 134 generally will comprise water, acetic acid, and PRC's, as well as quantities of methyl iodide and methyl acetate. The condensed heavy phase in decanter 134 will generally comprise methyl iodide, methyl acetate, and PRC's. The condensed heavy liquid phase in the decanter 134 can be conveniently recirculated, either directly or indirectly, to the reactor 104 via stream 118. For example, a portion of this condensed heavy liquid phase can be recirculated to the reactor, with a slip stream (not shown), generally a small amount, e.g., from 5 to 40 vol. %, or from 5 to 20 vol. %, of the heavy liquid phase being directed to a PRS. This slip stream of the heavy liquid phase may be treated individually or may be combined with the condensed light liquid phase stream 138 for further distillation and extraction of carbonyl impurities.

Although the specific compositions of the light phase stream 138 may vary widely, some preferred compositions are provided below in Table 1.

TABLE 1

Exemplary Light Phase
Compositions from Light Ends Overhead

|  | conc. (Wt.%) | conc. (Wt.%) | conc. (Wt.%) |
|---|---|---|---|
| HOAc | 1-40 | 1-25 | 5-15 |
| Water | 50-90 | 50-80 | 60-80 |
| PRC's | <5 | <3 | <1 |
| MeI | <10 | <5 | <3 |
| MeAc | 1-50 | 1-25 | 1-15 |

As shown in FIG. 1, the light phase exits decanter 134 via stream 138. A first portion, e.g., aliquot portion, of light phase stream 138 is recycled to the top of the light ends column 124 as reflux stream 140. A second portion, e.g., aliquot portion, of light phase stream 138 is directed outside of the primary purification train 108 to PRS 132, as discussed above and as shown by stream 142. A third portion, e.g., aliquot portion, of the light phase stream 138 optionally may be recycled to reactor 104 as shown by recycle stream 114.

Light ends column 124 also preferably forms residuum or bottoms stream 116, which comprises primarily acetic acid and water. Since light ends bottoms stream 116 typically will comprise some residual catalyst, it may be beneficial to recycle all or a portion of light ends bottoms stream 116 to reactor 104. Optionally, light ends bottoms stream 116 may be combined with the catalyst phase 110 from flasher 112 and returned together to reactor 104, as shown in FIG. 1.

As indicated above, in addition to the overhead phase, the light ends column 124 also forms an acetic acid sidedraw 128, which preferably comprises primarily acetic acid and water. In order to maintain an efficient product separation, it is important that the composition of the sidedraw 128 does not vary or fluctuate significantly during normal operation.

Optionally, a portion of the sidedraw 128 may be recirculated to the light ends column, preferably to a point below where sidedraw 128 was removed from light ends column, in order to improve the separation (not shown).

Since sidedraw 128 contains water in addition to acetic acid, sidedraw 128 from the light ends column 124 preferably is directed to drying column 130, in which the acetic acid and water are separated from one another. As shown, drying column 130, separates acetic acid sidedraw 128 into overhead stream 144 comprised primarily of water and bottoms stream 146 comprised primarily of acetic acid. Overhead stream 144 preferably is cooled and condensed in a phase separation unit, e.g., decanter 148, to form a light phase 150 and a heavy phase 122. As shown, a portion of the light phase is refluxed, as shown by stream 152 and the remainder of the light phase is returned to the reactor 104, as shown by stream 120. The heavy phase, which typically is an emulsion comprising water and methyl iodide, preferably is returned in its entirety to the reactor 104, as shown by stream 122, optionally after being combined with stream 120. Exemplary compositions for the light phase of the drying column overhead are provided below in Table 2.

TABLE 2

Exemplary Light Phase Compositions
from Drying Column Overhead

|  | conc. (Wt.%) | conc. (Wt.%) | conc. (Wt.%) |
|---|---|---|---|
| HOAc | 1-20 | 1-15 | 1-10 |
| Water | 50-90 | 60-90 | 70-90 |
| MeI | <10 | <5 | <3 |
| MeAc | 1-20 | 1-15 | 1-10 |

In certain embodiments, as discussed, minor amounts of an alkali component such as KOH can be added to sidedraw 128 via line 160 prior to entering the drying column 130. In other embodiments, the alkali component might also be added to the drying column 130 at the same height level as the stream 128 entering the drying column 130 or at a height above the height level height level as the stream 128 entering the drying column 130. Such addition can neutralize HI in the column.

Drying column bottoms stream 146 preferably comprises or consists essentially of acetic acid. In preferred embodiments, drying column bottoms stream 146 comprises acetic acid in an amount greater than 90 wt. %, e.g., greater than 95 wt. % or greater than 98 wt. %. In embodiments, this stream will also be essentially anhydrous, for example, containing less than 0.15 wt. % water, e.g., less than 0.12 wt. % water or less than 0.1 wt. % water. However, as discussed, the stream may contain varying levels of impurities.

Figure 2:
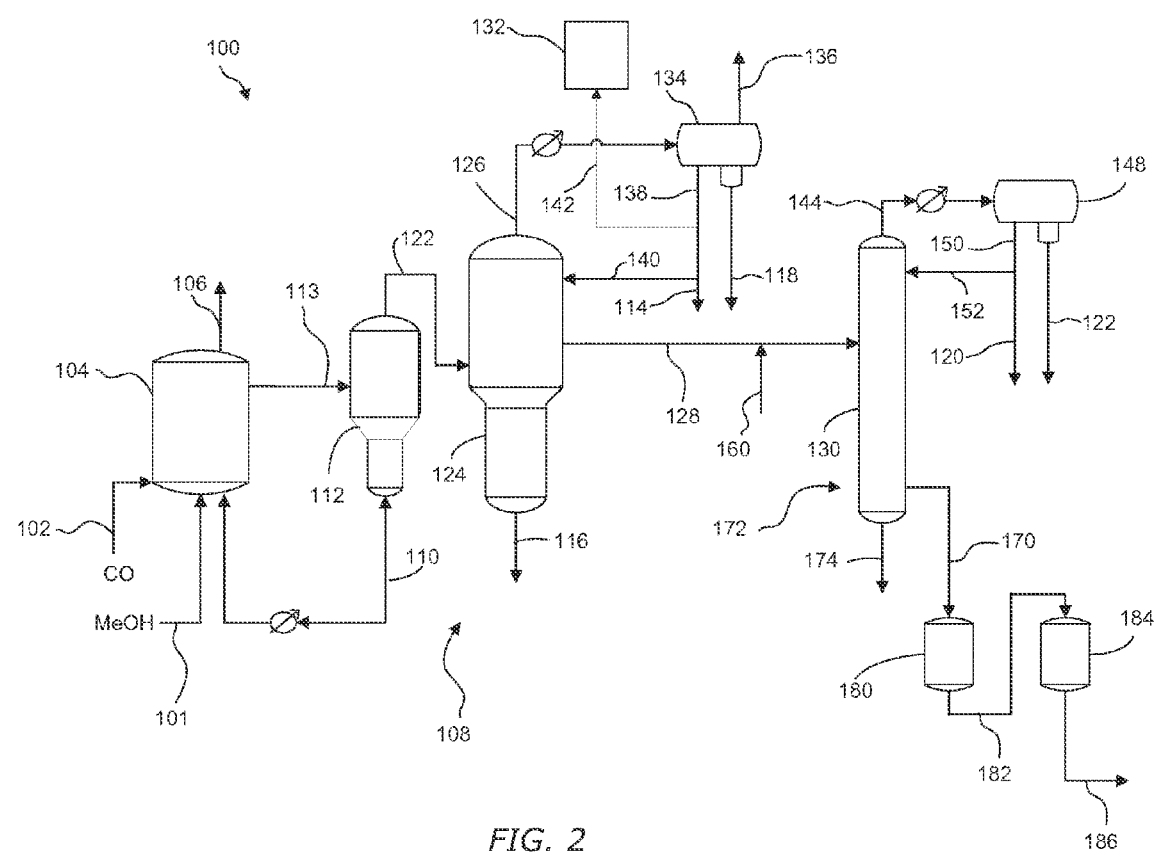
FIG. 2 illustrates another process for producing acetic acid with a metal functionalized fixed resin bed for iodide removal.

In FIG. 1, the crude acid product is withdrawn as a residue in drying column bottoms stream 146. As shown in FIG. 2, in certain embodiments, the crude acid product from the drying column 130 may be taken from a side stream 170 at a position slightly above the bottom 172 of the column 130. Side stream 170 may be withdrawn in the liquid or vapor phase. When withdrawn in the vapor phase further condensing and cooling may be necessary prior to removing alkaline contaminants, e.g., lithium contaminants. For example, the crude acid product may be taken as a side stream 170 from a lower part of the column, while a residue stream 174 from the base of the drying column 130 is withdrawn and removed or recycled. Side stream 170 contains the crude acetic acid product that is sent to cationic exchange resin to remove lithium. This can allow for the separation of a higher boiling point fraction from the crude acid product in residue stream 174. Residue stream 174 may be discarded or purged from the process 100.

In the present invention, the crude acid product is further processed, by passing through a series of metal functionalized iodide removal ion exchange resins, prior to being stored or transported for commercial use.

Iodide Removal Beds/Use of Ion Exchange Resins

According to the present process, carboxylic acid streams, e.g., acetic acid streams, that are contaminated with halides (e.g., iodides) and lithium may be contacted with an acid-form cationic exchange resin followed by a metal-exchanged ion exchange resin having acid cation exchange sites comprising at least one metal selected from the group consisting of silver, mercury, palladium and rhodium under a range of operating conditions. Preferably, the ion exchange resin compositions are provided in fixed beds. The use of fixed iodide removal beds to purify contaminated carboxylic acid streams is well documented in the art (see, for example, U.S. Pat. Nos. 4,615,806; 5,653,853; 5,731,252; and 6,225,498, which are hereby incorporated by reference in their entireties). Generally, a contaminated liquid carboxylic acid stream is contacted with the aforementioned ion exchange resin compositions, by flowing through a series of static fixed beds. The lithium contaminants are removed by the cationic exchanger in the acid form. The halide contaminants, e.g., iodide contaminants, are then removed by reaction with the metal of the metal-exchanged ion exchange resin to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

Similar iodide contamination issues may exist in acetic anhydride manufactured via a rhodium-iodide catalyst system. Thus, the inventive process may alternatively be utilized in the purification of crude acetic anhydride product streams.

Suitable acid-form cation exchangers for removing metal ion contaminants in the present invention may comprise strong acid cation exchange resins, for example strong acid macroreticular or macroporous resins, for example Amberlyst® 15 resin (DOW), Purolite C145, or Purolite CT145. The resin may also be an acid-form strong acid cation exchange mesoporous resin. Chelating resins and zeolites may also be used.

Suitably stable ion exchange resins utilized in connection with the present invention for preparing silver or mercury-exchanged resins for iodide removal typically are of the "RSO3H" type classified as "strong acid," that is, sulfonic acid, cation exchange resins of the macroreticular (macroporous) type. Particularly suitable ion exchange substrates include Amberlyst® 15, Amberlyst® 35 and Amberlyst® 36 resins (DOW) suitable for use at elevated temperatures. Other stable ion exchange substrates such as zeolites may be employed, provided that the material is stable in the organic medium at the conditions of interest, that is, will not chemically decompose or release silver or mercury into the organic medium in unacceptable amounts. Zeolite cationic exchange substrates are disclosed, for example, in U.S. Pat. No. 5,962,735, the disclosure of which is incorporated herein by reference.

At temperatures greater than about 50° C., the silver or mercury exchanged cationic substrate may tend to release small amounts of silver or mercury on the order of 500 ppb or less and thus the silver or mercury exchanged substrate is chemically stable under the conditions of interest. More preferably, silver losses are less than 100 ppb into the organic medium and still more preferably less than 20 ppb into the organic medium. Silver losses may be slightly higher upon start up. In any event, if so desired a bed of acid form cationic material may be placed downstream of the silver or mercury exchange material in addition to the bed of acid form cationic material upstream of the silver or mercury exchange material, to catch any silver or mercury released.

The pressures during the contacting steps with the exchange resins are limited only by the physical strength of the resins. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) and 118° C. (the boiling point of acetic acid). It is within the purview of those skilled in the art to determine analogous ranges for product streams comprising other carboxylic acid compounds. The temperature of the contacting step preferably is kept low enough to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin significant degrading (via the mechanism of acid-catalyzed aromatic desulfonation) at temperatures of 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for lithium and/or halide removal.

The configuration of the resin beds within an acetic acid purification train may vary, but the cationic exchanger should be upstream of the metal-exchanged resin. In a preferred embodiment, the resin beds are configured after a final drying column. Preferably the resin beds are configured in a position wherein the temperature of the crude acid product is low, e.g., less than 120° C. or less than 100° C. The stream contacting the acid-form cationic exchange resin and the stream contacting the metal-exchanged resin can be adjusted to the same or different temperatures. For example, the stream contacting the acid-form cationic exchange resin can be adjusted to a temperature of from 25° C. to 120° C., e.g., 25° C. to 85° C., 40° C. to 70° C., e.g., 40° C. to 60° C., while the stream contacting the metal-exchanged resin can be adjusted to a temperature of from 50° C. to 100° C., e.g., 50° C. to 85° C., 55° C. to 75° C., or 60° C. to 70° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

Referring back to FIG. 1, drying column bottoms stream 146 is first passed through cationic exchange resin bed 180 to remove lithium ions. Although one cationic exchange resin bed 180 is shown, it should be understood that a plurality of cationic exchange resin beds may be used in series or parallel. The cationic exchange bed may also remove other cations present in the stream, such as potassium, if added to drying column 130 as a potassium salt selected from the group consisting of potassium acetate, potassium carbonate, and potassium hydroxide, and corrosion metals. The resulting exchanged stream, e.g., intermediate acid product 182, then passes through a metal-exchanged ion exchange resin bed 184 having acid cation exchange sites comprising at least one metal selected from the group consisting of silver, mercury, palladium and rhodium to remove iodides from the stream to produce a purified product 186. Although one metal-exchanged ion exchange resin bed 184 is shown, it should be understood that a plurality of metal-exchanged ion exchange resin beds may be used in series or parallel. In addition to the resin beds, heat exchangers (not shown) may be located before either resin bed to adjust the temperature of the stream 146 and 182 to the appropriate temperature before contacting the resin beds. Similarly in FIG. 2, the crude acetic acid product is fed to cationic exchange resin bed 180 from side stream 170. Heat exchangers or condensers may be located before either resin bed to adjust the temperature of the stream 170 to the appropriate temperature before contacting the resin beds.

In one embodiment, the flow rate through the resin beds ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

A purified acetic acid composition is obtained as a result of the resin bed treatment. The purified acetic acid composition, in one embodiment, comprises less than 100 wppb, iodides, e.g., less than 90 wppb, less than 50 wppb, or less than 25 wppb. In one embodiment, the purified acetic acid composition comprises less than 100 wppb lithium, e.g., less than 50 wppb, less than 20 wppb, or less than 10 wppb. In terms of ranges, the purified acetic acid composition may comprise from 0 to 100 wppb iodides, e.g., from 0 to 50 wppb; and/or from 0 to 100 wppb lithium, e.g., from 1 to 50 wppb. In other embodiments, the resin beds remove at least 25 wt % of the iodides from the crude acetic acid product, e.g., at least 50 wt % or at least 75 wt %. In one embodiment, the resin beds remove at least 25 wt % of the lithium from the crude acetic acid product, e.g., at least 50 wt % or at least 75 wt %.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acetic acid comprising:
    carbonylating at least one member selected from the group consisting of methanol, dimethyl ether, and methyl acetate in the presence of 0.1 to less than 14 wt. % water, a rhodium catalyst, methyl iodide and iodide salts, to form a reaction medium in a reactor;
    separating the reaction medium into a liquid recycle stream and a vapor product stream comprising lithium cations; and
    separating the vapor product stream in a primary purification train consisting of a first column and second column, wherein the vapor product stream introduced to a first column to obtain a low-boiling overhead stream and side stream comprising acetic acid and lithium cations, and the side stream is introduced to a second column to obtain a residue comprising acetic acid, water, one or more organic iodides, and lithium in an amount from 0.01 ppm to 10 ppm.

2. The process of claim 1, wherein the residue comprises lithium in an amount from 0.05 ppm to 5 ppm.

3. The process of claim 1, wherein the residue further comprises quaternary nitrogen cations or phosphorous-containing cations.

4. The process of claim 1, further comprising reducing the lithium amount in the residue to less than 50 wppb.

5. The process of claim 1, further comprising reducing the lithium amount by greater than 90 wt. %.

6. The process of claim 1, further comprising reducing the amount of the one or more iodides in the residue.

7. The process of claim 1, wherein the one or more organic iodides comprises more than 10 ppb of $C_{10}$-$C_{14}$ alkyl iodides.

8. The process of claim 1, wherein the residues comprises from 20 ppb to 1.5 ppm of the one or more organic iodides.

9. The process of claim 1, wherein the residue comprises less than 0.2 wt. % water.

10. The process of claim 1, wherein the residue further comprises hydrogen iodide.

11. The process of claim 1, further comprising processing the residue to obtain a purified acetic acid composition comprise less than 100 ppb lithium and from 0 to 100 ppb iodides.

12. The process of claim 1, further comprising separating the low-boiling overhead stream into a light phase and heavy phase.

13. The process of claim 1, further comprising removing one or more PRC from light phase and/or heavy phase in a distillation column outside of the primary purification train.

* * * * *